United States Patent [19]

Bosies et al.

[11] Patent Number: 4,719,203

[45] Date of Patent: Jan. 12, 1988

[54] DIPHOSPHONIC ACID DERIVATIVES, PROCESSES FOR THE PREPARATION THEREOF AND PHARMACEUTICAL COMPOSITIONS CONTAINING THEM

[75] Inventors: Elmar Bosies, Weinheim; Rudi Gall, Hirschberg, both of Fed. Rep. of Germany

[73] Assignee: Boehringer Mannheim GmbH, Mannheim, Fed. Rep. of Germany

[21] Appl. No.: 930,331

[22] Filed: Nov. 12, 1986

[30] Foreign Application Priority Data

Nov. 13, 1985 [DE] Fed. Rep. of Germany ....... 3540150

[51] Int. Cl.$^4$ ...................... C07F 9/38; A61K 31/045; A61K 31/13; A61K 31/185
[52] U.S. Cl. .................... 514/108; 260/502.5 C; 514/89; 514/94; 514/95; 546/22; 548/112; 549/6; 558/158; 558/159; 558/161; 558/163
[58] Field of Search ................. 260/502.5 C; 514/108, 514/89, 94, 95; 546/22; 548/112; 549/6; 558/158, 159, 161, 163

[56] References Cited

U.S. PATENT DOCUMENTS

| | | | |
|---|---|---|---|
| 3,299,123 | 1/1967 | Fitch et al. | 260/502.5 C |
| 3,617,343 | 11/1971 | Kandler et al. | 260/502.5 C |
| 3,962,432 | 6/1976 | Schmidt-Dunker | 514/108 |
| 4,054,598 | 10/1977 | Blum et al. | 260/502.5 C |
| 4,064,164 | 12/1977 | Blum et al. | 260/502.5 C |
| 4,267,108 | 5/1981 | Blum et al. | 260/502.5 C |
| 4,304,734 | 12/1981 | Jary et al. | 260/502.5 C |
| 4,407,761 | 10/1983 | Blum et al. | 260/502.5 C |
| 4,624,947 | 11/1986 | Blum et al. | 260/502.5 C |

FOREIGN PATENT DOCUMENTS

1002355 2/1957 Fed. Rep. of Germany ... 260/502.5 C

Primary Examiner—J. E. Evans
Attorney, Agent, or Firm—Felfe & Lynch

[57] ABSTRACT

Diphosphonate compounds, processes for their preparation and pharmaceutical compositions containing them and being useful for treating calcium metabolism disorders. The diphosphonates are of the formula

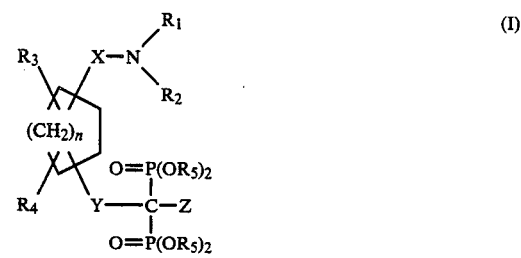

wherein $R_1$ and $R_2$ are hydrogen, acyl or alkyl which can be substituted by aryl, $R_3$ and $R_4$ are hydrogen or alkyl or $R_3$ and $R_4$ together represent lower alkylene, $R_5$ is a hydrogen atom or alkyl, X is a valency bond or alkylene, Y is a valency bond, alkylene or substituted alkylene, Z is hydrogen, hydroxyl or amino group optionally substituted by alkyl and n is 1, 2 or 3; and including the pharmacologically acceptable salts thereof.

20 Claims, No Drawings

DIPHOSPHONIC ACID DERIVATIVES, PROCESSES FOR THE PREPARATION THEREOF AND PHARMACEUTICAL COMPOSITIONS CONTAINING THEM

The present invention is concerned with new diphosphonic acid derivatives, processes for the preparation thereof and pharmaceutical compositions containing them.

Federal Republic of Germany Patent Specification No. 18 13 659 describes diphosphonic acid derivatives of which 1-hydroxyethane-1,1-diphosphonic acid has achieved importance as an agent for the treatment of Paget's disease. In Belgian Patent Specification No. 896,453 A, as well as in European Patent Specification No. 96931 A, there are described aminoalkane-1,1-diphosphonic acids as good calcium complex formers which can also be used for the treatment of increased bone resorption.

We have now found that aminocycloalkane-diphosphonic acids represent a hitherto unknown group of calcium complex formers which can also be used for the treatment of increased bone resorption and especially in cases where the formation and breakdown of bone is disturbed, i.e. they can be used for the treatment of diseases of the skeletal system, for example osteoporosis, Paget's disease, Bechterew's disease and the like.

However, on the basis of these properties, they can also be used in the therapy of bone metastases, urolithiasis and for the prevention of heterotopic ossification. Due to their influence on the calcium metabolism, they also form a basis for the treatment of rheumatoid arthritis, osteoarthritis and degenerative arthrosis.

Thus, according to the present invention, there are provided diphosphonic acid derivatives of the general formula:

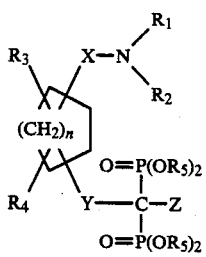
(I)

wherein $R_1$ and $R_2$, which can be the same or different, are hydrogen atoms or lower acyl or alkyl radicals which can be substituted by aryl, $R_3$ and $R_4$, which can be the same or different, are hydrogen atoms or lower alkyl radicals or $R_3$ and $R_4$ can together represent a lower alkylene radical, $R_5$ is a hydrogen atom or a lower alkyl radical, X is a valency bond or a lower, straight-chained or branched alkylene radical, Y is a valency bond, a lower, straight-chained or branched alkylene radical optionally substituted by $-NR_1R_2$, in which $R_1$ and $R_2$ have the same meaning as above, Z is a hydrogen atom, a hydroxyl group or an amino group optionally substituted by alkyl radicals and n is 1, 2 or 3; and the pharmacologically acceptable salts thereof.

The lower alkyl and alkylene radicals in substituents $R_1$–$R_5$, X and Y alone or as components of other substituents mean radicals containing up to 4 carbon atoms, preferably methyl, ethyl or isopropyl radicals or methylene, ethylene or propylidene radicals.

Acyl is a lower alkyl-CO radical and preferably an acetyl radical.

Aryl (Ar) preferably means a phenyl, pyridyl, imidazolyl or thienyl radical. By an aryl-substituted alkyl radical is to be understood especially a benzyl or pyridylmethyl radical.

$R_5$ is preferably a hydrogen atom.

n=1–3 represent the cyclopentyl, cyclohexyl or cycloheptyl radical, the cyclohexyl radical being preferred.

In the case of rings bridged by $R_3$–$R_4$, the norbornyl and the bicyclo[2.2.2]octyl radical is preferred.

The cycloalkanes can be present as stereisomeric mixtures or as pure cis- and trans-isomers.

Asymmetric carbon atoms present in X, Y or the rings can have the R-, S- or R,S-configuration.

The compounds of the present invention can be prepared by known processes:

I. When Z in general formula (I) represents a hydroxyl group, the compounds are preferably prepared in that:

(a) a carboxylic acid of the general formula:

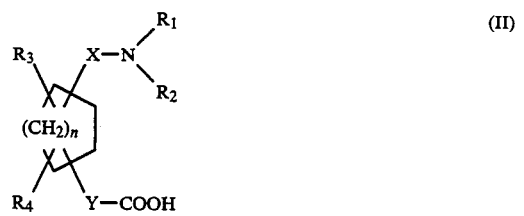
(II)

in which $R_1$–$R_4$, X, Y and n have the above-given meanings, is reacted with a mixture of phosphorous acid or phosphoric acid and a phosphorus halide, followed by saponification to the free diphosphonic acid; or (b) a carboxylic acid chloride of the general formula:

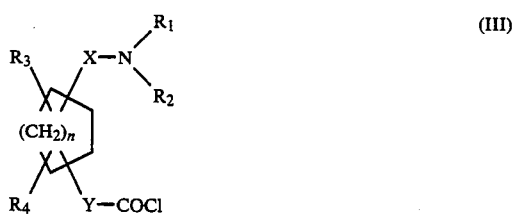
(III)

in which $R_1$–$R_4$, X, Y and n have the above given meanings and, if $-NR_1R_2$ is a primary or secondary amino group, this is protected and in which $R_1$ and $R_2$ together can also signify a phthaloyl radical, is reacted with a trialkyl phosphite of the general formula:

$$P(OR')_3 \qquad (IV)$$

in which R' is a lower alkyl radical, to give an acyl phosphonate of the general formula:

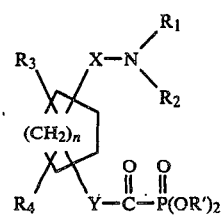

in which $R_1$–$R_4$, X, Y, n and R' have the above-given meanings, which is subsequently reacted with a dialkyl phosphite of the general formula:

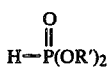

in which R' has the above-given meaning, to give a diphosphonate of the general formula:

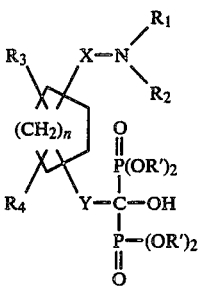

in which $R_1$–$R_4$, X, Y, n and R' have the above-given meanings, any protective groups possibly present are split off and the resultant tetraesters are optionally saponified to give the corresponding diesters or acids of general formula (I); or (c) a compound of the general formula:

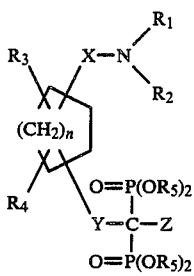

in which $R_3$, $R_4$, $R_5$, n, X and Y have the above-given meanings, $R_1$ and $R_2$ are each lower acyl or alkyl radicals which can be substituted by aryl or together represent a phthaloyl radical and Z is a primary amino group, is diazotised; or II. When Z in general formula (I) is an amino group optionally substituted by alkyl radicals, a carboxylic acid derivative of the general formula:

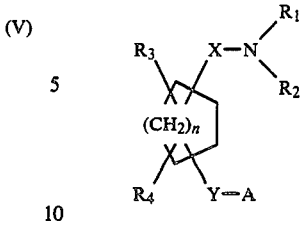

in which $R_1$–$R_4$, X, Y and n have the above-given meanings and A is a nitrile, imino ether or a carboxamide group optionally substituted on the nitrogen atom by lower alkyl, is reacted with a phosphorus compound of the general formula:

in which T is a halogen atom, a hydroxyl group or OR', in which R' has the above-given meaning, and optionally subsequently saponified; or III. When Z in general formula (I) is a hydrogen atom, a compound of the general formula:

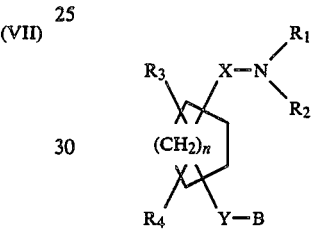

in which $R_1$–$R_4$, X, Y and n have the above-given meanings and if —$NR_1R_2$ is a primary or secondary amino group this is protected and in which $R_1$ and $R_2$ can together also represent a phthaloyl radical and B is a reactive residue, for example halogen or sulphonate, is reacted with a compound of the general formula:

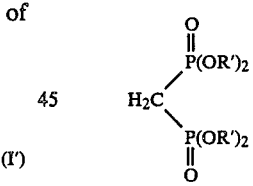

in which R' has the above-given meaning, to give a diphosphonate of the general formula:

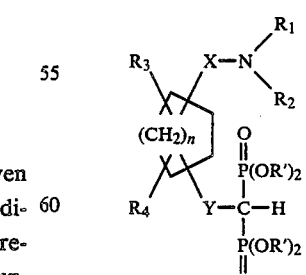

in which $R_1$–$R_4$, X, Y, n and R' have the above-given meanings, protective groups possibly present are split off and the resultant tetraesters are optionally saponified to diesters or acids of general formula (I); and, if desired, N-acyl substituents present are split off and subsequently, if desired, free amino groups are alkylated or acylated and the compounds obtained of general formula (I) are, if desired, converted into pharmacologically acceptable salts.

In the case of process III, the methylene-diphosphonic acid ester of general formula (XI) is used in the form of its sodium or potassium salt. For this purpose, it is reacted with sodium, potassium or the corresponding hydride in an inert solvent, for example benzene, toluene or dimethylformamide, at a temperature of from 0° to 40° C. and preferably of 25° C. The alkali metal salt is, without isolation, reacted with the appropriate halide or sulphonate, the temperature here used being from 20° to 110° C.

In the case of process II, the nitriles of general formula (VIII) are reacted with phosphorous acid at a temperature of from 110° to 180° C. The reaction can be carried out without or in the presence of aprotic solvents, for example diglycol dimethyl ether or diglycol diethyl ether. However, the nitriles can also be reacted with a phosphorus trihalide, for example phosphorus tribromide or phosphorus trichloride, in an inert solvent, for example dioxan or tetrahydrofuran, optioanlly with the addition of water, at a temperature of from 20° to 80° C. Iminoethers of general formula (VIII) can be reacted with dialkyl phosphites, preferably in the presence of equimolar amounts of sodium, in an inert solvent, for example diethyl ether, dioxan or also benzene, whereby, as a rule, the reaction takes place at the reflux temperature of the solvent used. Acid amides of general formula (VIII) can be reacted in inert solvents, for example halogenated hydrocarbons or ethers, such as diethyl ether, with a mixture of phosphorus pentahalide/phosphorous acid or also of oxalyl chloride/trialkyl phosphite.

The carboxylic acids of general formula (II) used in process (Ia) are reacted with 1 to 2 and preferably 1.5 mole of phosphorous acid or phosphoric acid and 1 to 2 and preferably 1.5 mole of phosphorus trihalide at a temperature of from 80° to 130° C. and preferably of from 100° to 110° C. The reaction can also be carried out in the presence of diluents, for example halogenated hydrocarbons, especially chlorobenzene or tetrachloroethane, or also dioxan. The subsequent hydrolysis takes place by boiling with water but preferably with semiconcentrated hydrochloric or hydrobromic acid.

In the case of process (Ib), the acid chloride of general formula (III) is reacted with the trialkyl phosphite of general formula (IV) at a temperature of from 0° to 60° C. and preferably of from 20° to 40° C. It is possible to work without a solvent or also in the presence of an inert solvent, for example, diethyl ether, tetrahydrofuran or dioxan, or also of a halogenated hydrocarbon, for example methylene chloride. The acyl phosphonate of general formula (V) formed as intermediate can be isolated or further worked up directly. The subsequent reaction is carried out in the presence of a weak base, preferably of a secondary amine, such as dibutylamine, at a temperature of from 0° to 60° C. and preferably of from 10° to 30° C.

In the case of process (Ic), a 1-amino-1, 1-diphosphonic acid of general formula (I') is reacted in aqueous solution with sodium nitrite in excess, preferably of 4 mole, at a temperature of from 0° to 60° C. and preferably of from 20° to 40° C.

The protective groups used in the above-described processes are known from peptide chemistry and are described in detail in, for example Houben-Weyl, Volume 15/1. Preferred protective groups include aralkoxy-carbonyl radicals, especially the benzyloxycarbonyl radical, and alkoxycarbonyl radicals, preferably the tert.-butoxycarbonyl radical. However, there can also be used a formyl, trityl, trifluoroacetyl or trichloroethoxycarbonyl radical.

The splitting off of the protective groups after the reaction has taken place can be carried out in conventional manner. Benzyloxycarbonyl and trityl radicals can be removed by catalytic hydrogenation in the presence of noble metal catalysts, for example palladium on charcoal, and tert.-butoxycarbonyl radicals by the action of strong acids, for example hydrochloric acid or trifluoroacetic acid. Trichloroethoxycarbonyl radicals can be split off reductively, for example by the action of zinc in glacial acetic acid and the phthaloyl radical can be removed in an acidic medium or also by hydrazinolysis.

The tetraalkyl esters possibly obtained in the case of processes (Ib), II and III can be saponified to give the diesters or the free tetraacids. The saponification to diesters takes place, as a rule, by treating the tetraalkyl esters with an alkali metal halide, preferably sodium iodide, in an appropriate solvent, for example acetone, at ambient temperature. There is hereby formed the symmetrical diester/disodium salt which, if desired, can be converted by means of an acidic ion exchanger into the diester/diacid. The saponification to free diphosphonic acids takes place, as a rule, by boiling with hydrochloric and hydrobromic acid. However, splitting can also be carried out with a trimethylsilyl halide, preferably the bromide or iodide. On the other hand, the free diphosphonic acids can again be converted into the tetraalkyl esters by boiling with orthoformic acid alkyl esters. The free diphosphonic acids of general formula (I) can be isolated as the free acids or also in the form of their mono- or dialkali metal salts. As a rule, the alkali metal salts can be readily purified by reprecipitation from water/methanol or water/acetone.

The compounds of general formula (I) can possibly be subsequently converted from one into another. Thus, for example, they can be alkylated or acylated. By means of the hydrogenolytic splitting off of an N-benzyl radical, there can, for example, be prepared the corresponding unsubstituted compounds of general formula (I).

As pharmacologically acceptable salts, there are, in particular, used the alkali metal and ammonium salts which can be prepared in the usual manner, for example by neutralisation of the compounds with inorganic or organic bases, for example sodium or potassium hydrogen carbonate, aqueous sodium hydroxide solution, aqueous potassium hydroxide solution, aqueous ammonia solution or amines, for example trimethylamine or triethylamine.

The new compounds of general formula (I) according to the present invention and the salts thereof can be administered enterally or parenterally in liquid or solid form. For this purpose, there can be used all conventional forms of administration, for example tablets, capsules, dragees, syrups, solutions, suspensions and the like. As injection medium, it is preferred to use water which contains the additives usual in the case of injection solutions, for example stabilising agents, solubilising agents and buffers. Additives of this kind include, for example, tartrate and citrate buffers, ethanol, complex formers (such as ethylene-diamine-tetraacetic acid and the non-toxic salts thereof) and high molecular weight polymers (such as liquid polyethylene oxide) for viscosity regulation. Liquid carrier materials for injection solutions must be sterile and are preferably placed into ampoules. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage can depend upon various factors, such as the mode of administration, species, age and/or individual state of health. The dosage to be administered daily can be from 1 to 1000 mg./human and preferably 10° to 200° mg./human and can be taken in one or more doses.

Preferred compounds according to the present invention, apart from those mentioned in the Examples, and the compounds derivable by combination of all meanings given in the claims, include the following diphosphonates, as well as the methyl and ethyl esters thereof:

3-(2-aminocycloheptyl)-1-hydroxypropane-1,1-diphosphonic acid
3-(2-N-benzylaminocyclohexyl)-1-hydroxypropane-1,1-diphosphonic acid
2-(2-aminocyclohexyl)-1-hydroxyethane-1,1-diphosphonic acid
1[3-(2-aminoethyl)-cyclohexyl]-1-hydroxymethane-1,1-diphosphonic acid
1-[2-(2-aminoethyl)-cyclohexyl]-1-hydroxymethane-1,1-diphosphonic acid
1-(2-aminomethylcyclohexyl)-1-hydroxymethane-1,1-diphosphonic acid
3-(1-aminocyclopentyl)-1-hydroxypropane-1,1-diphosphonic acid
3-(1-aminocycloheptyl)-1-hydroxypropane-1,1-diphosphonic acid
cis-3-(2-benzylaminocyclohexyl)-1-hydroxypropane-1,1-diphosphonic acid
trans-3-(2-benzylaminocyclohexyl)-1-hydroxypropane-1,1-diphosphonic acid
3-(3-amino-2-norbornyl)-1-hydroxypropane-1,1-diphosphonic acid
2-(3-amino-2-norbornyl)-1-hydroxyethane-1,1-diphosphonic acid
3-(3-amino-2-bicyclo[2,2,2]octyl)-1-hydroxypropane-1,1-diphosphonic acid
2-(3-amino-2-bicyclo[2,2,2]octyl)-1-hydroxyethane-1,1-diphosphonic acid
3-amino-3-(2-aminocyclohexyl)-1-hydroxypropane-1,1-diphosphonic acid
2-amino-3-(2-aminocyclohexyl)-1-hydroxypropane-1,1-diphosphonic acid
1-hydroxy-3-(2-methylaminocyclohexyl)-propane-1,1-diphosphonic acid
1-amino-3-(2-aminocyclohexyl)-propane-1,1-diphosphonic acid
2-(2-aminocyclohexyl)-ethane-1,1-diphosphonic acid
1-hydroxy-3-[2-(2-pyridylmethylamino)-cyclohexyl]-propane-1,1-diphosphonic acid
3-(2-aminocyclohexyl)-propane-1,1-diphosphonic acid
3-(1-N,N-dimethylaminocyclohexyl)-1-hydroxypropane-1,1-diphosphonic acid The following Examples, which are given for the purpose of illustrating the present invention, show some of the process variants which can be used for preparing the compounds according to the present invention. The structures of these compounds have been verified by H- and P-NMR spectroscopy, the purity by means of P-NMR spectroscopy, thin layer electrophoresis (cellulose, oxalate buffer of pH 4.0) and by means of C, H, N, P and Na analysis. For the characterisation of the individual compounds there are given the $M_{rel}$ values (relative mobility), referred to pyrophosphate ($M_{rel}=1.0$).

1 EXAMPLE 1

2-(4-Aminocyclohexyl)-1-hydroxyethane-1,1-diphosphonic acid

β-Nitrophenylacetic acid is hydrogenated in ethanol in the presence of Raney nickel to give, in a yield of 72% of theory, p-aminophenylacetic acid (m.p. 185°–189° C.). This is hydrogenated in solution is hydrochloric acid in the presence of a platinum catalyst to give p-aminocyclohexylacetic acid in the form of the hydrochloride in a yield of 23% of theory; m.p. 164–168° C.

1.7 g. p-Aminocyclohexylacetic acid hydrochloride is suspended in 10 ml. chlorobenzene, 1 g. phosphorous acid is added thereto, the mixture is heated to 100° C. and, while stirring, 2.3 ml. phosphorus trichloride are added dropwise thereto. After stirring for 12 hours at 100° C., the reaction mixture is cooled, the solvent is decanted off and the residue is mixed with 15 ml. 6N hydrochloric acid and stirred for 6 hours at 100° C. The suspension is cooled, mixed with acetone, the solution is evaporated and the residue is brought to crystallisation with methanol. There is thus obtained 1.2 g. (45% of theory) of the diphosphonic acid as the hemihydrate; m.p. 223°–228° C. (decomp.); $M_{rel}=0.22$.

1.57 g of this diphosphonic acid is dissolved in 20.7 ml. 1N aqueous sodium hydroxide solution, mixed with 1 ml. acetic anhydride and left to stand at ambient temperature for 2 days. The reaction solution is then applied to an "Amberlite" column (Ir 120 H+form) and eluted with water which is then evaporated. The oily residue is brought to crystallisation with methanol; m.p. 208°–213° C. (decomp.). There is thus obtained 0.6 g. (33% of theory) 2-(4-acetylaminocyclohexyl)-1-hydroxyethane-1,1-diphosphonic acid monohydrate; $M_{rel}=0.61$.

EXAMPLE 2

3-(4-Aminocyclohexyl)-1-hydroxypropane-1,1-diphosphonic acid p-Aminocyclohexylpropionic acid is obtained from 4-nitrocinnamic acid by hydrogenation (yield 26% of theory; m.p. 195°–201° C.) and reacted, in the manner described in Example 1, with phosphorus trichloride/-phosphorous acid. The desired diphosphonic acid is obtained in a yield of 45% of theory (m.p. 255°–258° C.) and crystallises with 1.5 mole water of crystallisation; $M_{rel}=0.22$.

EXAMPLE 3

1-(4-Aminocyclohexyl)-1-hydroxymethane-1,1-diphosphonic acid p-Aminobenzoic acid is hydrogenated in the presence of a platinum catalyst to give a yield of 67% of theory of 4-aminocyclohexylcarboxylic acid; m.p. 256°–258° C. The reaction with phosphorus trichloride/phosphorous acid takes place in the manner described in Example 1 and gives the desired compound in a yield of 32% of theory; m.p. 235°–238° C. (decomp.); $M_{rel}=0.27$.

EXAMPLE 4 trans-1-(4-Aminoethylcyclohexyl)-1-hydroxymethane-1,1-diphosphonic acid monosodium salt trans-4-Aminomethylcyclohexane carboxylic acid (obtainable from Aldrich) is reacted, as described in Example 1, with phosphorus trichloride/phosphorous acid, the diphosphonic acid (m.p. 220°–225° C.), obtained in a yield of 33% of theory, is suspended in water, brought to a pH of 5 with 1N aqueous sodium hydroxide solution, precipitated with acetone and brought to crystallisation with methanol; m.p. 275°–294° C. Yield of the monosodium salt 90% of theory; $M_{rel}=0.26$.

By stirring the tetrasodium salt of this diphosphonic acid in water with acetic anhydride at ambient temperature and subsequent treatment with "Amberlite" as described in Example 1, there is obtained, in a yield of 44% of theory, 1-(4-acetyl-aminomethylcyclohexyl)-1-hydroxymethane-1,1-diphosphonic acid as the hemihydrate; m.p. 164° C. sinters, 190° C. decomp.; $M_{rel}=0.59$.

EXAMPLE 5

2-(4-N,N-Dimethylaminocyclohexyl)-1-hydroxyethane-1,1-diphosphonic acid disodium salt.

The p-aminocyclohexylacetic acid described in Example 1 is mixed in aqueous solution with formalin solution and hydrogenated in the presence of palladium-charcoal to give 4-N,N-dimethylaminocyclohexylacetic acid; yield 24% of theory; m.p. sinters at 163° C., melts at 179° C.

The reaction to give the diphosphonic acid takes place in the manner described in Example 1. Yield 83% of theory; m.p. 60°–65° C. (decomp.).

With the calculated amount of 1N aqueous sodium hydroxide solution, there is obtained the disodium salt as the monohydrate in a yield of 43% of theory; m.p. at 350° C. bubbling; $M_{rel}=0.24$.

EXAMPLE 6

2-(4-Aminomethylcyclohexyl)-1-hydroxyethane-1,1-diphosphonic acid

The p-aminophenylacetic acid described in Example 1 is converted into p-cyanophenylacetic acid by diazotisation in the manner described in J. Chem. Soc., 1941, 745, the yield being 47% of theory; m.p. 138°–141° C. It is then hydrogenated in the presence of platinum catalyst in hydrochloric acid solution to give 4-aminomethylcyclohexylacetic acid; yield 63% of theory; m.p. 120–123° C. (decomp.).

The diphosphonic acid is obtained therefrom as the hemihydrate in a yield of 35% of theory in a manner analogous to that described in Example 1; m.p. 208°14 214° C. (decomp.); $M_{rel}=0.24$.

EXAMPLE 7.

2-(3-Aminocyclohexyl)-1-hydroxyethane-1,1-diphosphonic acid

In a manner analogous to that described in Example 1, 3-aminocyclohexylacetic acid is reacted to give the diphosphonic acid dihydrate; yield 11% of theory; m.p. 223°–228° C. (decomp.); $M_{rel}=0.26$.

The 3-aminocyclohexylacetic acid used as starting material is obtained in the following manner: 3-nitrobenzaldehyde is reduced in the manner described in J.A.C.S., 71, 123, with sodium borohydride in methanol to give 3-nitrobenzyl alcohol; yield 97% of theory; greasy crystals. This is reacted according to J.A.C.S., 52, 1643 with thionyl chloride to give 3-nitrobenzyl chloride; yield 42% of theory; m.p. 40°–42° C., after recrystallisation from ligroin. Reaction with potassium cyanide, carried out in the manner described in Chem. & Ind., 1935, 105, gives a yield of 58% of theory of 3-nitrophenylacetic acid; m.p. 101°–107° C. From this, by hydrogenation in the presence of platinum catalyst, there is obtained the desired 3-aminocyclo-hexylacetic acid; yield 28% of theory; m.p. 188°–200° C. (decomp.).

EXAMPLE 8

2-(3-Aminomethylcyclohexyl)-1-hydroxyethane-1,1-diphosphonic acid

The 3-nitrophenylacetic acid described in Example 7 is hydrogenated in methanol in the presence of palladium-charcoal to give a yield of 99% of theory of 3-aminophenylacetic acid (m.p. 116°–121° C.). In a manner analogous to that described for the p-compound (see Example 6), there is obtained therefrom, by diazotisation, 3-cyanophenylacetic acid (yield 45% of theory; m.p. 93°–98° C. (decomp.)) and by hydrogenation in dilute hydrochloric acid in the presence of platinum catalyst there is obtained 3-aminomethylcyclohexylacetic acid; yield 66% of theory; m.p. 127°–130° C. The diphosphonic acid is obtained therefrom by means of phosphorus trichloride/phosphorous acid in the manner described in Example 1 in the form of the monohydrate; yield 28% of theory; m.p. 216°–221° C. (decomp.); $M_{rel}=0.27$.

EXAMPLE 9

3-(3-Aminocyclohexyl)-1-hydroxypropane-1,1-diphosphonic acid m-Cinnamic acid is hydrogenated in hydrochloric acid solution in the presence of palladium-charcoal and the β-(3-aminophenyl)-propionic acid thus obtained is further hydrogenated in the presence of platinum catalyst; yield 56% of theory β-(3-aminocyclohexyl)-propionic acid; m.p. 175°–185° C. (decomp.).

The diphosphonic acid is obtained therefrom, in the manner described in Example 1, in a yield of 66% of theory as the hemihydrate; m.p. 221°–223° C. (decomp.); $M_{rel}=0.23$.

EXAMPLE 10

3-(2-Acetylaminocyclohexyl)-1-hydroxypropane-1,1-diphosphonic acid o-Nitrocinnamic acid is hydrogenated in 1N aqueous sodium hydroxide solution in the presence of Raney nickel. To the filtrate is subsequently added acetic anhydride, the reaction mixture is left to stand overnight and the resultant suspension is filtered off with suction, washed and dried. There is obtained, in a yield of 57% of theory, o-acetylaminohyocinnamic acid; m.p. 139°–143° C.

After hydrogenation in hydrochloric acid solution using a platinum catalyst, there is obtained 3-(2-acetylaminocyclohexyl)-propionic acid in the form of a cis,trans mixture with a trans proportion of 11%; yield 50% of theory; m.p. 116°–121° C.

The preparation of the diphosphonic acid takes place in the manner described in Example 1 but, after the hydrochloric acid hydrolysis, the product obtained, which is partly deacetylated, is reacted with acetic anhydride to give uniform 3-(2-acetylaminocyclohexyl)-1-hydroxypropane-1,1-diphosphonic acid in the form of the monohydrate; yield 38% of theory; m.p. above 83° C. foaming; $M_{rel} = 0.56$.

EXAMPLE 11

2-(2-Aminomethylcyclohexyl)-1-hydroxyethane-1,1-diphosphonic acid

In a manner analogous to that described in Example 1, (2-aminomethylcyclohexyl)-acetic acid is reacted with phosphorus trichloride/phosphorous acid to give the diphosphonic acid hemihydrate. Yield 4% of theory after purification on an Amberlite column (Ir 120 H+form); m.p. 196° C. foaming up; $M_{rel} = 0.32$.

The starting material is obtained in the following manner: 2-indanone oxime is obtained in a yield of 81% of theory in the manner described in J. Org. Chem., 9, 386; m.p. 145°–148° C. The rearrangement to the lactam of 2-aminomethylphenylacetic acid is achieved in the manner described in J. Chem. Soc., 65, 490 by means of phosphorus pentachloride, the yield being 69% of theory. Ring opening to give 2-aminomethylphenylacetic acid takes place by boiling for 2 hours in concentrated hydrochloric acid, the yield being 22% of theory; m.p. 151°–155° C. (hydrochloride). Finally, by hydrogenating in the presence of a platinum catalyst in hydrochloric acid solution, there is obtained a yield of 98% of theory of the hydrochloride of (2-aminomethylcyclohexyl)-acetic acid as a foaming product.

EXAMPLE 12

1-(3-Aminomethylcyclohexyl)-1-hydroxymethane-1,1-diphosphonic acid

In the manner described in J. prakt. Chem., 125, 43, m-cyanobenzoic acid is prepared from m-aminobenzoic acid by diazotisation, the yield being 52% of theory; m.p. 210°–212° C. By hydrogenation in acetic acid solution in the presence of palladium-charcoal, there is obtained m-aminomethylbenzoic acid and by further hydrogenation in the presence of a platinum catalyst in hydrochloric acid solution, there is obtained 3-aminomethylcyclohexanecarboxylic acid in the form of greasy crystals, the yield being quantitative.

The diphosphonic acid is prepared in a manner analogous to that described in Example 1. It is obtained as the monohydrate in a yield of 33% of theory; m.p. 208°–212° C.; $M_{rel} = 0.32$.

EXAMPLE 13 cis-3-(2-Aminocyclohexyl)-1-hydroxypropane-1,1-diphosphonic acid

From the cis-trans mixture of 3-(2-acetylaminocyclohexyl)-propionic acid described in Example 10, by recrystallisation from water there is obtained the pure cis-compound (yield 32% of theory; m.p. 131°–133° C.), the reaction of which with phosphorus trichloride/phosphorous acid takes place analogously to Example 1. The course of the splitting off of the acetyl radical by heating in hydrochloric acid is monitored by means of thin layer electrophoresis.

EXAMPLE 14

1-(4-(2-Aminoethyl)-cyclohexyl)-1-hydroxymethane-1,1-diphosphonic acid

In a manner analogous to that described in Example 1, from 4-(2-aminoethyl)-cyclohexanecarboxylic acid there is obtained the title compound in a yield of 32% of theory; m.p. 226°–230° C.; $M_{rel} = 0.21$.

The starting material is obtained in the following manner: p-bromomethylbenzoic acid (m.p. 215°–218° C.) is obtained from p-toluic acid and N-bromosuccinimide (see J. Org. Chem., 18, 708) in a yield of 66% of theory. After esterification with methanol and thionyl chloride (yield 84% of theory), it is reacted with potassium cyanide (see J. Org. Chem., 17, 1037) to give methyl p-cyanomethylbenzoate, the yield being 59% of theory; m.p. 56°–59° C. Hydrogenation in the presence of palladium-charcoal gives a yield of 64% of theory of methyl 4-(2-aminoethyl)-benzoate; m.p. 209°–216° C. (decomp.). Further hydrogenation in the presence of platinum catalyst and subsequent saponification with 2N aqueous sodium hydroxide solution at ambient temperature gives a yield of 65% of theory of 4-(2-aminoethyl)-cyclohexanecarboxylic acid; m.p. 218°–224° C. (decomp.).

EXAMPLE 15 cis-3-(2-Aminocyclohexyl)-1-hydroxypropane-1,1-diphosphonic acid

This compound, which is identical with that prepared according to Example 13, can also be obtained by reacting the hydrochloride of cis-3-(2-aminocyclohexyl)-propionic acid with phosphorus trichloride/phosphorous acid analogously to Example 1 and purification of the hydrolysis product by ion exchanger chromatography. The yield is 10% of theory; m.p. 204° C. sinters, above 208° C. foaming up.

The starting material is prepared in the following manner: o-nitrocinnamic acid is hydrogenated according to Bull. Soc. chim. France, 1964, 2617, to give a yield of 93% of theory of 1,2,3,4-tetrahydroquinolin-2-one (m.p. 150°–155° C.) which is hydrogenated in the presence of platinum catalyst in hydrochloric acid solution to give decahydroquinolin-2-one in a yield of 79% of theory. From the cis,trans mixture (about 10% trans) there is obtained, by recrystallising twice from water, the pure cis compound in a yield of 23% of theory; m.p. 158 –163° C. The lactam ring is opened by boiling with hydrochloric acid, the yield being 59% of theory; m.p. 161°–163° C.

EXAMPLE 16

3-(1-Aminocyclohexyl)-1-hydroxypropane-1,1-diphosphonic acid 19.1 g. 1-Aza-spiro(4,5)decan-2-one (prepared as described in J. Org. Chem., 22, 832) are boiled for 90 hours in 190 ml. concentrated hydrochloric acid. After cooling, the reaction mixture is filtered and evaporated and the residue is reprecipitated with methanol/diethyl ether. There are obtained 17.5 g. (68% of theory) of the hydrochloride of 3-(1-aminocyclohexyl)-propionic acid; m.p. 183° C. sinters; 188°–192° C. melts with decomposition. 7 g. thereof are mixed with 5.5 g. phosphorous acid and, after melting at 80° C., mixed dropwise with 5.9 ml. phosphorus trichloride. After stirring for 8 hours at 80° C., 43 ml. 6N hydrochloric acid are added thereto, the temperature is increased to 100° C. and stirring continued for a further 8 hours. The yellowish suspension is then filtered hot, the filtrate is evaporated and the residue, a colourless oil, is stirred into 2 liters of acetone. The precipitate obtained is filtered off with suction and washed with acetone and diethyl ether.

There are obtained 4.6 g. (43% of theory) of product which are dissolved in a little water. Purification takes place by fractionation on an Amberlite IR-120 column (H+form). The individual fractions are tested electrophoretically for purity. After combining the pure fractions, the aqueous solution is again evaporated and again precipitated with acetone. There are obtained 2.9 g. (27% of theory) of white crystals; m.p. 143° C. sinters, 155°-158° C. foaming up; $M_{rel}=0.29$.

EXAMPLE 17 trans-3-(2-Aminocyclohexyl)-1-hydroxypropane-1,1-diphosphonic acid trans-3-(2-Aminocyclohexyl)-propionic acid hydrochloride is prepared in a yield of 62% of theory in the manner described in Chemical Abstracts, 50, 9410 i. The reaction with phosphorous acid/phosphorus trichloride takes place in the manner described in the previous Example, as well as the working up and purification. The yield is 10% of theory; m.p. 90° C. sinters, at 170° C. foaming up, at 220° C. decomposition; $M_{rel}=0.27$.

EXAMPLE 18

3-(2-Dimethylaminocyclohexyl)-1-hydroxypropane-1,1-diphosphonic acid 3-(2-Dimethylaminocyclohexyl)-propionic acid is reacted, as described in Example 16, with phosphorous acid/phosphorus trichloride, hydrolysed and worked up to give the pure product. There is obtained a yield of 40% of theory of the dihydrate which decomposes above 65° C.; $M_{rel}=0.27$.

The starting material is prepared as follows: 3-(2-aminophenyl)-propionic acid, obtained from sodium o-nitrocinnamate by hydrogenation in the presence of palladium-charcoal, is further hydrogenated with formalin in the presence of triethylamine. The resulting mixture is separated on a silica gel column (elution agent: methylene chloride-methanol-acetic acid 9:1:0.2 v/v/v). The desired compound, 3-(2-dimethylaminophenyl)-propionic acid, is obtained as an oil in a yield of 30% of theory. The hydrogenation of the aromatic nucleus is carried out in glacial acetic acid-hydrochloric acid in the presence of platinum catalyst and gives the desired starting material in a yield of 44% of theory; m.p. 118° C. sinters, 128°-138° C.

EXAMPLE 19

3-(2-Amino-3-methylcyclohexyl)-1-hydroxypropane-1,1-diphosphonic acid

3-Methyl-2-nitrobenzaldehyde, prepared according to Berichte, 47, 406, is reacted with malonic acid in pyridine with the addition of piperidine to give 3-methyl-2-nitrocinnamic acid; yield 64% of theory; m.p. 230°-235° C., after recrystallisation from methanol. After hydrogenation thereof in aqueous sodium hydroxide solution in the presence of palladium catalyst, 2 mole of acetic anhydride are added thereto and the reaction product is purified on an Amberlite IR-120 column (H+form). There is thus obtained, in a yield of 75% of theory, 3-(2-acetylamino-3-methyl-phenyl)-propionic acid; m.p. 110° C. sinters, 117°-120° C. This is then reacted with phosphorous acid/phosphorus trichloride analogously to Example 16.

According to the method of working up described therein, there is obtained, in a yield of 9% of theory, 3-(2-amino-3-methylphenyl)-1-hydroxypropane-1,1-diphosphonic acid; m.p. 208° C. sinters, 215°-219° C. decomposition. The hydrogenation of the aromatic nucleus is carried out in aqueous solution in the presence of platinum catalyst and gives, after purification on an Amberlite IR-120 column (H+form), a yield of 67% of theory of the desired product; m.p. 133° C. sinters, 166° C. foaming up; $M_{rel}=0.31$.

EXAMPLE 20

3-(2-Aminocyclopentyl)-1-hydroxypropane-1,1-diphosphonic acid.

Starting from 3-(2-aminocyclopentyl)-propionic acid hydrochloride (described in C.A. 60, 4111 a), there is obtained, in a manner analogous to that described in Example 16, the desired compound in a yield of 12% of theory as a cis, trans mixture (63:37); m.p. 105°-125° C. (decomp.); $M_{rel}=0.21$.

EXAMPLE 21

3-(2-Aminocyclohexyl)-1-hydroxypropane-1,1-diphosphonic acid.

Starting from 3-(2-acetylaminocyclohexyl)-1-hydroxypropane-1,1-diphosphonic acid, the acetyl radical is completely eliminated by heating to 100° C. for 70 hours in 6N hydrochloric acid. The diphosphonic acid is purified by chromatographing on Amberlite IR-120 (H+form) to give 3-(2-aminocyclohexyl)-1-hydroxypropane-1,1-diphosphonic acid sesquihydrate in the form of a cis, trans mixture (ratio as in the starting material). Yield 23% of theory; m.p. 163° C., foaming up; $M_{rel}=0.31$.

In Vivo Testing on Calcium Metabolism Disorders

Male Wistar rats from our own breeding weighing about 160 g were thyroparathyroidectomized on day 1. On day 5, the success of the operation was controlled by measuring calcemia after a night fasting. From that day on, all the animals were group-fed, that means all of them ate the same quantity of food. Furthermore, the animals received then daily for 3 days 2 subcutaneous injections, on containing 25 μg of a synthetic retinoid, the other one the bisphosphonate to be tested. Additionally, all animals were given 2 μg of thyroxine the first and last day of treatment. 24 h after the last injection of the retinoid and the biphosphonates and after one night fasting, blood was taken by retroorbital puncture under ether anesthesia. Plasma calcium was then analyzed by means of atomic absorption.

The bisphosphonates were given first at a dose of 0.1 mg P/kg in a volume of 2 ml/kg, the less active also at 1 and 10 mg P/kg.

The Table shows the various doses compared with 1-hydroxyethane-1,1-diphosphonate acid.

| | mg P/kg | | |
|---|---|---|---|
| Example No. | 0.1 | 1 | 10 |
| 1 | o | ++ | o |
| 3 | (+) | 0 | |
| 7 | (+) | (+) | o |
| 8 | o | o | (+) |
| 9 | o | (+) | (+) |
| 10 | o | ++ | (+) |
| 11 | + | +++ | (+) |
| 13 | +++ | | |
| 16 | +++ | | |
| 20 | +++ | | |
| 1-hydroxy-ethane-1,1-diphosphonic acid | o | o | (+) |

-continued

| | mg P/kg | | |
|---|---|---|---|
| Example No. | 0.1 | 1 | 10 |
| (from DE-OS 18 13 659) | | | | o = Depression of Hypercalcaemie - 0,99 bis + 0,99 mg %
(+) = Depression of Hypercalcaemie 1,0 bis 1,99 mg %
+ = Depression of Hypercalcaemie 2.0 bis 2,99 mg %
++ = Depression of Hypercalcaemie 3.0 bis 3,99 mg %
+++ = Depression of Hypercalcaemie >4.0 mg %

It will be understood that the specification and examples are illustrative but not limitative of the present invention and that other embodiments within the spirit and scope of the invention will suggest themselves to those skilled in the art.

What is claimed is:

1. A diphosphonate of the formula

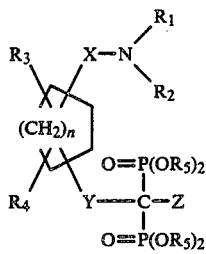

(I)

wherein $R_1$ and $R_2$, which can be the same or different, are hydrogen, $C_2-C_5$ acyl, $C-C_4$ alkyl or $C-C_4$ alkyl substituted by aryl, pyridyl, imidazolyl or thienyl, $R_3$ and $R_4$, which can be the same or different, are hydrogen or $C-C_4$ alkyl or $R_3$ and $R_4$ together represent alkylene with up to 4 carbons, $R_5$ is hydrogen or $C-C_4$ alkyl, X is a valency bond or alkylene with up to 4 carbons, Y is a valency bond, $C-C_4$ alkylene or $C-C_4$ alkylene substituted by $-NR_1R_2$, in which $R_1$ and $R_2$ have the same meanings as above, Z is hydrogen, or hydroxy and n is 1, 2 or 3; or the pharmacologically salts thereof.

2. The diphosphonate of claim 1, wherein $R_1$ and $R_2$, which can be the same or different, are hydrogen, methyl or acetyl, $R_3$ and $R_4$, which can be the same or different, are hydrogen or methyl, $R_5$ is hydrogen, X and Y, which can be the same or different, are valency bonds, methylene or ethylene Z, is a hydroxy group and n is 1 or 2, or the pharmacologically acceptable salts thereof.

3. The diphosphonate of claim 1 wherein $R_1$ is methyl, ethyl, isopropyl or acetyl.

4. The diphosphonate of claim 1 wherein $R_1$ is $C-C_4$ alkyl substituted by phenyl, pyridyl, imidazolyl or thienyl.

5. The diphosphonate of claim 1 wherein X is a valence bond, methylene or ethylene.

6. The diphosphonate of claim 1 wherein $R_5$ is hydrogen, Y is methylene or ethylene and Z is hydroxy.

7. The diphosphonate of claim 1 wherein Y is methylene or ethylene.

8. The diphosphonate of claim 1 designated 3-(2-acetylaminocyclohexyl)-1-hydroxypropane-1, 1-diphosphonic acid.

9. The diphosphonate of claim 1 designated 2-(2-aminomethylcyclohexyl)-1-hydroxyethane-1, 1-diphosphonic acid.

10. The diphosphonate of claim 1 designated cis-3-(2-aminocyclohexyl)-1-hydroxypropane-1, 1-diphosphonic acid.

11. The diphosphonate of claim 1 designated 3-(1-aminocyclohexyl)-1-hydroxypropane-1, 1-diphosphonic acid.

12. The diphosphonate of claim 1 designated 3-(2-aminocyclohexyl)-1-hydroxypropane-1, 1-diphosphonic acid.

13. The diphosphonate of claim 1 designated 3-(2-Aminocyclopentyl)-1-hydroxypropane-1, 1-diphosphonic acid.

14. A pharmaceutical composition comprising an effective amount of diphosphonate of claim 1 in a pharmaceutically acceptable carrier for treating calcium metabolism disorders.

15. The pharmaceutical composition of claim 14 containing 1 to 1000 mg of said diphosphonate.

16. The pharmaceutical composition of claim 14 containing 10 to 200 mg of said diphosphonate.

17. The pharmaceutical composition of claim 14 wherein said diphosphonate is
3-(2-acetylaminocyclohexyl)-1-hydroxypropane-1, 1-diphosphonic acid;
2-(2-aminomethylcyclohexyl)-1-hydroxyethane-1, 1-diphosphonic acid;
cis-3-(2-aminocyclohexyl)-1-hydroxypropane-1, 1-diphosphonic acid;
3-(1-aminocyclohexyl)-1-hydroxypropane-1, 1-diphosphonic acid;
3-(2-aminocyclohexyl)-1-hydroxypropane-1, 1-diphosphonic acid; or
3-(2-Aminocyclopentyl)-1-hydroxypropane-1, 1-diphosphonic acid.

18. A method for treating calcium metabolism disorders comprising administering, enterally or parenterally, the pharmaceutical composition of claim 14.

19. A method for treating calcium metabolism disorder comprising administering, enterally or parenterally, an effective amount of the diphosphonate of claim 1.

20. The method of claim 19 wherein 1 to 1000 mg of the diphosphonate, are administered.

* * * * *

UNITED STATES PATENT AND TRADEMARK OFFICE
CERTIFICATE OF CORRECTION

PATENT NO.  : 4,719,203

DATED       : January 12, 1988

INVENTOR(S) : Elmar Bosies, et al.

It is certified that error appears in the above-identified patent and that said Letters Patent is hereby corrected as shown below:

Column 5, line 23:  change "tribomide" to -- tribromide --.

Column 9, line 56:  change "208°14" to -- 208°- --.

Column 10, line 59:  change "o-acetylaminohyocinnamic" to -- o-acetylaminohydrocinnamic --.

Column 15, lines 32, 35, 36, 38 and 53:  change "C-$C_4$" to -- $C_1$-$C_4$ --.

Signed and Sealed this

Eleventh Day of October, 1988

*Attest:*

DONALD J. QUIGG

*Attesting Officer*   *Commissioner of Patents and Trademarks*